United States Patent [19]

Borror et al.

[11] Patent Number: 4,720,449

[45] Date of Patent: Jan. 19, 1988

[54] THERMAL IMAGING METHOD

[75] Inventors: Alan L. Borror, Andover; Ernest W. Ellis, Carlisle, both of Mass.

[73] Assignee: Polaroid Corporation, Cambridge, Mass.

[21] Appl. No.: 861,377

[22] Filed: May 14, 1986

Related U.S. Application Data

[63] Continuation-in-part of Ser. No. 740,889, Jun. 3, 1985, abandoned.

[51] Int. Cl.$^4$ ................................................. G03C 1/72
[52] U.S. Cl. ..................................... 430/338; 430/343; 430/945; 430/955; 430/964; 503/218; 503/221; 503/222; 548/207
[58] Field of Search ............... 430/964, 338, 332, 343, 430/955, 945; 503/221, 222, 218; 548/207, 467, 455; 564/42, 44, 51, 56

[56] References Cited

U.S. PATENT DOCUMENTS

| | | | |
|---|---|---|---|
| Re. 29,168 | 4/1977 | Jenkins et al. | 430/522 |
| 3,488,705 | 1/1970 | Fox et al. | 430/53 |
| 3,832,212 | 8/1974 | Jenkins et al. | 430/495 |
| 4,097,288 | 6/1978 | Lawton | 430/343 |
| 4,122,089 | 10/1978 | Kimura et al. | 346/221 |
| 4,380,629 | 4/1983 | Yamashita et al. | 430/495 |
| 4,500,897 | 2/1985 | Matsuda et al. | 503/218 |

FOREIGN PATENT DOCUMENTS 47-29662  8/1972  Japan ................................. 346/221

OTHER PUBLICATIONS

Kosar, J., Light-Sensitive System: Chemistry and Application of Nonsilver Halide Photographic Processes, New York, NY John Wiley and Sons, Inc., 1976, pp. 402–419.

*Primary Examiner*—Won H. Louie
*Assistant Examiner*—Mark R. Buscher

[57] ABSTRACT

A thermal imaging method is provided which comprises heating imagewise a di- or triarylmethane compound possessing within its di- or triarylmethane structure an aryl group substituted in the ortho position to the meso carbon atom with a moiety ring-closed on the meso carbon atom directly through a nitrogen atom, which nitrogen atom is also bound to a group with a masked acyl substituent that undergoes fragmentation upon heating to liberate the acyl group for effecting intramolecular acylation of said nitrogen atom to form a new group in the ortho position whereby the di- or triarylmethane compound is rendered colored in an imagewise pattern corresponding to said imagewise heating.

16 Claims, No Drawings

THERMAL IMAGING METHOD

CROSS-REFERENCE TO RELATED APPLICATION

This application is a continuation-in-part of copending application Ser. No. 740,889 filed June 3, 1985, now abandoned.

BACKGROUND OF THE INVENTION

1. Field of the Invention

This invention relates to heat-sensitive recording elements useful for making color images, to a method of imaging using said elements and to novel organic compounds useful as the image-forming materials in said heat-sensitive recording elements.

2. Description of the Prior Art

A variety of thermal imaging systems for producing color images have been proposed, and several have been mentioned in Kosar, J., Light-Sensitive Systems: Chemistry and Application of Nonsilver Halide Photographic Processes, New York, John Wiley and Sons, Inc., 1965, pp. 402-19. In one type of heat sensitive recording system, a first sheet containing a first reagent is superposed with a second sheet containing a second reagent and one of the reagents is melted or vaporized by the imagewise application of heat and transferred for reaction with the other reagent to form a color image. In another type of "transferring system", images are formed by sequentially transferring two or more dyes carried on separate donor sheets to a common receptor sheet by melting or volatilization. In thermal imaging systems of the "self-containing" type, a single sheet is used and the imagewise heating of the heat-sensitive sheet produces a color image, for example, by rendering a coating layer transparent to reveal the color of a background layer, by initiating the chemical reaction of two or more reagents to form a colored product or by bleaching, coloring or changing the color of a single reagent.

A number of compounds of the latter type, that is, single compounds which undergo a color change upon application of heat have been disclosed. U.S. Pat. No. 3,488,705 discloses thermally unstable organic acid salts of triarylmethane dyes useful in electrophotographic elements as sensitizing dyes that are decomposed and bleached upon heating. U.S. Pat. No. 3,745,009 reissued as U.S. Pat. No. Re. 29,168 and U.S. Pat. No. 3,832,212 disclose heat-sensitive compounds for thermography containing a heterocyclic nitrogen atom substituted with an —OR group, for example, a carbonate group that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds which undergo coloration or bleaching, reversibly or irreversibly via ring-opening and ring-closing in response to activating energies such as light, heat, electric potential, and copending U.S. Patent application Ser. No. 646,771 of Alan L. Borror, Ernest W. Ellis and Donald A. McGowan filed Sept. 4, 1984, now U.S. Pat. No. 4602263 discloses organic compounds that undergo color formation or color bleaching by an irreversible unimolecular fragmentation of at least one thermally unstable carbamate moiety, for example, triarylmethane compounds including bridged triarylmethane compounds comprising a carbamate moiety, such as,

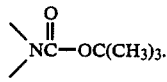

SUMMARY OF THE INVENTION

The present invention is concerned with thermal imaging systems employing certain di- and triarylmethane compounds comprising a moiety ring-closed on the meso carbon atom, i.e., the methane carbon atom, that are substantially colorless initially and become colored as a result of a thermal fragmentation reaction to unmask a group for effecting an intramolecular nucleophilic substitution reaction whereby the di- or triarylmethane compound becomes irreversably ring-opened. In a preferred embodiment, the ring-closed moiety is bonded to the meso carbon atom directly through a nitrogen atom and upon heating undergoes intramolecular acylation on said nitrogen atom whereby a new moiety is formed which cannot bond to the meso carbon atom and which irreversibly "traps" the di- or triarylmethane compound in an open, colored form.

Because the subject compounds undergo an intramolecular reaction to effect a color change, coloration can be achieved without the need for transferring a reagent or for contacting two reagents, and because coloration can be achieved at moderately elevated temperatures, any conventional heating means for effecting imagewise heating may be employed. Also, di- and triarylmethane compounds useful in the subject thermal imaging systems may be selected to provide a wide range of colors including black as may be desired not only in the production of monochromes and bichromes but in the production of full color images as well.

It is, therefore, the primary object of the present invention to provide a method of thermal imaging for producing color images.

It is another object of the present invention to provide heat-sensitive recording elements useful in said method.

It is yet another object of the present invention to provide a new class of heat-sensitive compounds useful in the subject thermal imaging systems.

Other objects of the invention will in part be obvious and will in part appear hereinafter.

The invention accordingly comprises the methods involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

In accordance with the present invention, a method of thermal imaging is provided which comprises heating imagewise a heat-sensitive element comprising a support carrying at least one layer of a colorless di- or triarylmethane compound possessing within its di- or triarylmethane structure an aryl group substituted on a carbon atom in the ortho position to the meso carbon atom with a moiety ring-closed on the meso carbon atom to form a 5- or 6-membered ring, said moiety possessing a nitrogen atom bonded directly to said meso carbon atom and said nitrogen atom being bound to a group, e.g., a phenyl group substituted with a masked acyl substituent that undergoes fragmentation upon heating to liberate the acyl group for effecting intramolecular acylation of said nitrogen atom to form a new group in the ortho position that cannot bond to the meso carbon atom, said imagewise heating effecting the formation of said new group in the ortho position whereby said di- or triarylmethane compound is rendered colored in an imagewise pattern corresponding to said imagewise heating. Preferably, the masked acylating substituent is a masked carbonyl group that undergoes thermal fragmentation in the presence of heat to liberate a reactive carbonyl group for effecting said intramolecular acylation reaction.

Typical diarylmethane and triarylmethane compounds that may be used in the present invention are the novel color-forming compounds represented by the formula

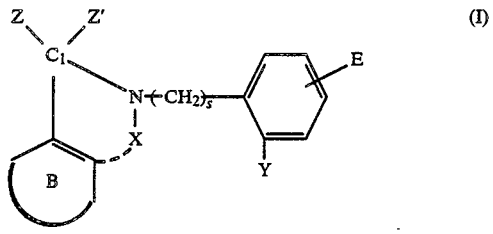

(I)

wherein ring B represents a carbocyclic aryl ring, e.g., of the benzene or naphthalene series or a heterocyclic aryl ring, e.g., pyridine or pyrimidine; $C_1$ represents the meso carbon atom; X represents

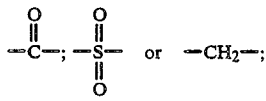

Y represents a substituent that undergoes fragmentation upon heating to liberate a group capable of acylating said nitrogen atom; E is hydrogen, an electron donating group, an electron-withdrawing group or a group, either an electron-donating group or an electron-neutral group, that undergoes fragmentation upon heating to liberate a new group that renders the overall reaction more efficient, preferably an electron-withdrawing group; s is 0 or 1; and Z and Z' taken individually represent the moieties to complete the auxochromophoric system of a diarylmethane or a triarylmethane dye when said N-containing ring is open and Z and Z' when taken together represent the bridged moieties to complete the auxochromophoric system of a bridged triarylmethane dye when said N-containing ring is open. In a preferred embodiment, B represents a benzene ring and Z and Z' taken individually represent the aryl moieties, the same or different, to complete the auxochromophoric system of a triarylmethane dye when said N-containing ring is open and Z and Z' when taken together represent the bridged aryl moieties to complete the auxochromophoric system of a bridged triarylmethane dye when said N-containing ring is open. Usually, at least one of Z and Z' whether taken individually or together possesses as an auxochromic substituent, a nitrogen, oxygen or sulfur atom or a group of atoms containing nitrogen, oxygen or sulfur.

In the triarylmethane compounds represented in formula I above, the aryl moieties Z and Z', when taken individually, may be the same or different and typically represent heterocyclic aryl groups containing nitrogen, oxygen or sulfur as the heterocyclic atom, particularly N-heterocyclic aryl groups such as julolidin-3-yl, indol-3-yl, pyrr-2-yl, carbazol-3-yl, and indolin-5-yl wherein the N atom of the indolyl, pyrryl, carbazolyl and indolinyl groups may be substituted with hydrogen or alkyl having 1 to 6 carbon atoms, or the aryl moieties Z and Z' typically may be carbocyclic aryl, particularly phenyl or naphthyl groups which include an appropriately positioned auxochromic substituent, i.e., an atom or group that produces an auxochromic effect, which substituent is usually positioned para to the meso carbon atom. Typically, Z and Z' when taken together represent aryl groups bridged by a heteroatom, such as, oxygen, sulfur or nitrogen to form, for example, 4H-chromeno [2,3-C] pyrazole ad particularly represent carbocyclic aryl groups, such as, phenyl groups bridged with a heteroatom, preferably oxygen, sulfur or nitrogen substituted with hydrogen or an alkyl group having 1 to 6 carbon atoms to provide a xanthene, thioxanthene or an acridine dye, which dyes possess an auxochromic substituent(s) para to the meso carbon atom, i.e., in the 3-position or in the 3,6-positions or meta and para to the meso carbon atom, i.e., in the 3,7-positions.

In the diarylmethane compounds, one of Z and Z' may be heterocyclic aryl or carbocyclic aryl as discussed above and the other of Z and Z' may be, for example, phenoxy, thiophenoxy, alkoxy containing 1 to 20 carbon atoms, alkylthio containing 1 to 20 carbon atoms, —N,N-(disubstituted)amino wherein each said substituent may be alkyl containing 1 to 20 carbon atoms, carbocyclic aryl containing 6 to 12 carbon atoms, aralkyl containing 7 to 15 carbon atoms particularly phenyl- and naphthyl-substituted alkyl or alkaryl containing 7 to 15 carbon atoms particularly alkyl-substituted phenyl and naphthyl. Representative alkyl groups include methyl, butyl, hexyl and octadecyl and representative aryl groups include phenyl and naphthyl. Representative alkaryl groups include p-octylphenyl, o-methylnaphthyl and p-hexylphenyl, and representative aralkyl groups include phenethyl, benzyl and naphthylmethyl.

Examples of useful auxochromic substituents include —$OR_1$ wherein $R_1$ is hydrogen, alkyl usually having 1 to 6 carbon atoms, aralkyl usually having 7 to 15 carbon atoms, alkaryl usually having 7 to 15 carbon atoms or carbocyclic aryl usually having 6 to 12 carbon atoms; —$SR_2$ wherein $R_2$ has the same meaning given for $R_1$; —$NR_3R_4$ wherein $R_3$ and $R_4$ each represent hydrogen, alkyl usually having 1 to 6 carbon atoms, β-substituted ethyl, cycloalkyl usually having 5 to 7 carbon atoms, aralkyl usually having 7 to 15 carbon atoms, alkaryl usually having 7 to 15 carbon atoms or

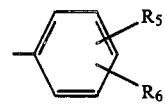

wherein $R_5$ and $R_6$ each are hydrogen, alkyl usually having 1 to 6 carbon atoms, halo such as chloro, bromo, fluoro and iodo, nitro, cyano, alkoxycarbonyl wherein said alkoxy has 1 to 6 carbon atoms, sulfonamido ($-NHSO_2R_0$), sulfamoyl ($-SO_2NHR_0$), sulfonyl ($-SO_2R_0$), acyl ($-COR_0$) or carbamyl ($-CONR_0$) wherein $R_0$ usually is alkyl having 1 to 6 carbon atoms, benzyl or phenyl and $R_3$ and $R_4$ taken together represent the atoms necessary to complete a heterocyclic ring usually piperidino, pyrrolidino, N-methylpiperidino, morpholino or

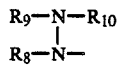

wherein q is an integer 2 to 5 and $R_7$ has the same meaning as $R_5$,

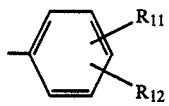

wherein $R_8$ and $R_9$ each are hydrogen, alkyl usually having 1 to 6 carbon atoms or

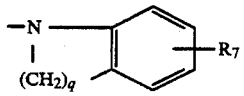

wherein $R_{11}$ and $R_{12}$ have the same meaning as $R_5$ and $R_6$ and $R_{10}$ is $-COR_{13}$, $-CSR_{13}$ or $-SO_2R_{13}$ wherein $R_{13}$ is hydrogen, alkyl usually having 1 to 6 carbon atoms, phenyl, $-NH_2$, $-NHR_{14}$, $-N(R_{14})_2$ or $-OR_{14}$ wherein $R_{14}$ is hydrogen, alkyl usually containing 1 to 6 carbon atoms or phenyl. Representative alkyl groups include methyl, ethyl, propyl, butyl and hexyl. Representative β-substituted ethyl groups include β-methoxymethoxyethyl and β-2'-tetrahydropyranyloxyethyl. Representative aralkyl groups include phenyl and naphthyl-substituted alkyl, such as, benzyl, phenethyl and naphthylmethyl and representative alkaryl groups include alkyl-substituted phenyl and naphthyl, such as, o-methylphenyl, o-methylnaphthyl and p-hexylphenyl. Representative carbocyclic aryl groups include phenyl and naphthyl and representative cycloalkyl groups include cyclopentyl, cyclohexyl and cycloheptyl. It will be appreciated that the auxochromic substituent(s) will be selected for a given diarylmethane, triarylmethane or bridged triarylmethane compound to provide the desired chromophore color upon opening of the N-containing ring and to achieve facile color formation.

Representative electron-donating groups for E include alkyl groups such as methyl, ethyl, t-butyl and hexyl, alkoxy groups such as methoxy, ethoxy, propoxy and butoxy, and amino, (monoalkyl)amino and (dialkyl)amino wherein said alkyls each contain 1 to 6 carbon atoms. Representative electron-withdrawing groups include cyano, dibenzylsulfonamido, dimethylsulfonamido, methylsulfonyl, phenylsulfonyl, p-tolylsulfonyl, carboxy, acetyl, carboethoxy, carbamyl, isothiocyano, benzoyl, trifluoromethyl and halo, e.g., chloro, bromo, fluoro and iodo. Useful electron-donating or electron-neutral groups that undergo fragmentation upon heating to liberate an electron-withdrawing group include

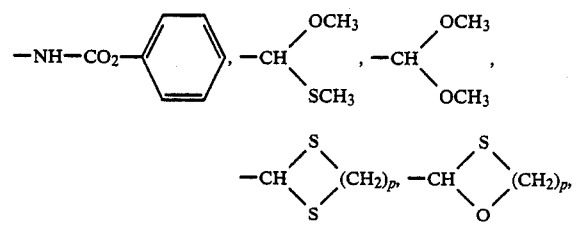

wherein p is an integer 1 to 4, $-CH-O-CH_2-O-R'$ and

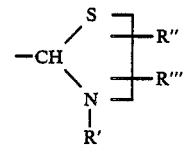

wherein R' is alkyl usually having 1 to 20 carbon atoms, aryl usually having 6 to 12 carbon atoms, aralkyl usually having 7 to 15 carbon atoms and alkaryl usually having 7 to 15 carbon atoms and R" and R''' each are hydrogen, alkyl usually having 1 to 6 carbon atoms, aryl having 6 to 12 carbon atoms, aralkyl usually having 7 to 15 carbon atoms and alkaryl usually having 7 to 15 carbon atoms. Typical alkyl, aryl, aralkyl and alkaryl groups for R', R" and R''' are those mentioned above.

As used herein and as well known in the art, an electron-withdrawing group is a group having a positive sigma value. An electron-donating group is a group having a negative sigma value and an electron-neutral group is a group having a sigma value of 0. In addition to the groups specified above, a number of other groups together with their sigma values are listed in Lang's Handbook of Chemistry and in H. H. Jaffe, A Reexamination of the Hammett Equation, Chem. Reviews, 1953, pp. 222–23. It will be understood that the electron-donating and the electron-neutral groups selected to provide an electron-withdrawing group will undergo fragmentation under the same heating conditions, i.e., in the same temperature range as required for the fragmentation reaction that unmasks the group for effecting the intramolecular nucleophilic substitution reaction.

In addition to the auxochromic substituents, Z and/or Z' and/or the ring B of the ring-closing moiety may possess one or more additional substituents as may be desired that do not interfere with the intended utility for the dye. Typical substituents include carboxy; hydroxy; cyano; thiocyano; mercapto; sulfo; nitro; sulfonamido ($-NHSO_2R_0$); sulfamoyl ($-SO_2NHR_0$); sulfonyl ($-SO_2R_0$); acyl ($-COR_0$); carbamyl ($-CONR_0$); halomethyl such as trifluoromethyl; alkyl usually having 1 to 20 carbon atoms such as methyl, octyl, hexadecyl; alkoxy usually having 1 to 20 carbon atoms such as methoxy, ethoxy, propoxy and butoxy; alkoxycarbonyl having 1 to 6 carbon atoms such as methoxy- and ethoxycarbonyl; aralkyl usually having 7 to 15 carbon atoms, for example, phenyl or naphthyl-substituted alkyl such as benzyl, phenethyl and naphthylmethyl; alkaryl usually having 7 to 15 carbon atoms, for example, alkyl-substituted phenyl or naphthyl such as o-methylphenyl, o-methylnaphthyl and p-hexylphenyl; aralkyloxy usually having 7 to 15 carbon atoms, for example, phenyl or naphthyl-substituted alkoxy, such as benzyloxy, phenethyloxy and naphthylmethyloxy; aryloxy usually containing 6 to 12 carbon atoms such as phenoxy and naphthoxy; thioalkyl groups usually having 1 to 20 carbon atoms such as methylthio, ethylthio and hexylthio; thioaryl and thioaralkyl groups containing up to 15 carbon atoms such as phenylthio, naphthylthio, benzylthio and phenethylthio, halo such as chloro, bromo, fluoro and iodo; amino including mono- and disubstituted amino such as $-NR_8R_9$ wherein $R_8$ and $R_9$ each are hydrogen, alkyl usually having 1 to 20 carbon atoms, aralkyl usually having 7 to 15 carbon atoms, alkaryl usually having 7 to 15 carbon atoms, and carbocyclic aryl usually having 6 to 12 carbon atoms; and a fused substituent such as a fused benzene ring.

Preferred compounds of the present invention are those represented by the formula

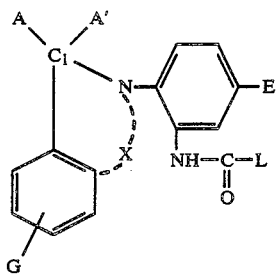
(II)

wherein $C_1$ represents the meso carbon atom; X represents

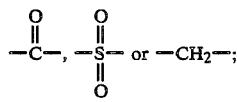

E is hydrogen, an electron-donating group, an electron-withdrawing group or a group, either an electron-donating group or an electron-neutral group, that undergoes fragmentation upon heating to liberate an electron-withdrawing group; L is a leaving group that departs upon thermal fragmentation to unmask —N=C=O; G is hydrogen, alkyl having 1 to 6 carbon atoms, alkoxy having 1 to 6 carbon atoms, alkoxycarbonyl having 1 to 6 carbon atoms, carboxy, cyano, thiocyano, nitro, sulfo, sulfonamido, sulfamoyl, sulfonyl, acyl, carbamyl, halo, —OR wherein R is hydrogen, alkyl having 1 to 6 carbon atoms, benzyl or phenyl, —$SR^0$ wherein $R^0$ has the same meaning as R or —$NR^5R^6$ wherein $R^5$ and $R^6$ each are hydrogen, alkyl having 1 to 6 carbon atoms, β-substituted ethyl, benzyl or phenyl; A and A', the same or different, are selected from phenyl substituted in the 4-position with —$OR^1$ wherein $R^1$ has the same meaning as R, —$SR^2$ wherein $R^2$ has the same meaning as R or —$NR^5R^6$ wherein $R^5$ and $R^6$ have the same meaning given above and substituted in the 2-, 3-, 5- and 6-positions with hydrogen, alkyl having 1 to 6 carbon atoms, alkoxy having 1 to 6 carbon atoms or chloro or substituted in the 5- and 6-positions with a fused benzene ring; indol-3-yl substituted in the 1 and 2 positions with hydrogen, alkyl having 1 to 6 carbon atoms, benzyl or phenyl; pyrr-2-yl substituted in the 1-position with hydrogen, alkyl having 1 to 6 carbon atoms, benzyl or phenyl; and carbazol-3-yl substituted in the 9-position with hydrogen, alkyl having 1 to 6 carbon atoms, benzyl or phenyl; and A and A' taken together represent phenyl groups bridged by a heteroatom selected from oxygen, sulfur and nitrogen substituted with hydrogen or alkyl having 1 to 6 carbon atoms to form xanthene, thioxanthene or acridine (a) substituted in the 3- and 6-positions with a group, the same or different, selected from —$OR^3$ wherein $R^3$ has the same meaning as R, —$SR^4$ wherein $R^4$ has the same meaning as R and —$NR^7R^8$ wherein $R^7$ is hydrogen or alkyl having 1 to 6 carbon atoms and $R^8$ is alkyl having 1 to 6 carbon atoms, benzyl or

wherein $R^9$ and $R^{10}$ each are hydrogen, alkyl usually having 1 to 6 carbon atoms, alkoxy having 1 to 6 carbon atoms, chloro, nitro, cyano, alkoxycarbonyl wherein said alkoxy has 1 to 6 carbon atoms, sulfonamido, sulfamoyl, sulfonyl, acyl, or carbamyl and $R^9$ and $R^{10}$ taken together represent indolino and

wherein $R^{11}$ and $R^{12}$ each are hydrogen, alkyl having 1 to 6 carbon atoms or

wherein $R^{14}$ and $R^{15}$ have the same meaning as $R^9$ and $R^{10}$ and $R^{13}$ is —$COR^{16}$ wherein $R^{16}$ is hydrogen, alkyl having 1 to 6 carbon atoms or phenyl and substituted in the 1-, 2-, 4-, 5-, 7- and 8-positions with hydrogen, alkyl having 1 to 6 carbon atoms, alkoxy having 1 to 6 carbon atoms or chloro or (b) substituted in the 3-position with —$NR^{17}R^{18}$ wherein $R^{17}$ is hydrogen, alkyl having 1 to 6 carbon atoms, cycloalkyl having 5 to 7 carbon atoms, benzyl or phenyl and $R^{18}$ is alkyl having 1 to 6 carbon atoms, cycloalkyl having 5 to 7 carbon atoms, benzyl or phenyl and $R^{17}$ and $R^{18}$ taken together represent piperidino, pyrrolidino, N-methylpiperidino or indolino and (1) substituted in the 7- and 8-positions with a fused benzene ring or (2) substituted in the 7-position with hydrogen, —$NR^{17}R^{18}$ wherein $R^{17}$ and $R^{18}$ have the same meaning given above, alkyl having 1 to 6 carbon atoms, alkoxy having 1 to 6 carbon atoms or chloro and substituted in the 1-, 2-, 4-, 5-, 6- and 8-positions with hydrogen, alkyl having 1 to 6 carbon atoms, alkoxy having 1 to 6 carbon atoms or chloro. Preferably, X is

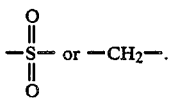

Leaving groups are well known and various leaving groups have been reported by Charles J. M. Stirling. Acc. Chem. Res. 12,198 (1979) and Charles J. M. Stirling, et al., J. Chem. Soc. Chem. Commum., 941 (1975). Examples of leaving groups that can be employed as L include imidazolyl; —SMe; —SPh; —SO₂Me; —SO₂Ph; —SePh; —OPh; —OMe; —P(O)(OEt)₂; —C(Me)₂NO₂, —N(Me)Ts; —N(Me)Ac; —N(Ph)Ac; —N(Ph)Ts; —N(Ph)CO₂CH₂Ph; and —N(Me)CO₂Ph wherein Me, Et, Ph, Ac and Ts represent methyl, ethyl, phenyl, acetyl and tosyl, respectively. The Ph and Ts groups may be substituted with one or more substituents, for example, alkyl, alkoxy, halo, carboxy, nitro, cyano, —SO₂alkyl, —SO₂phenyl, tosyl and N,N-(dialkyl)amino. Preferably, L is phenoxy unsubstituted or substituted with carboxy, nitro, cyano, halo, such as, chloro, bromo, iodo or fluoro, alkyl having 1 to 6 carbon atoms, alkoxy having 1 to 6 carbon atoms, N,N-(dialkyl)amino wherein said alkyl contains 1 to 6 carbon atoms, —SO₂phenyl, —SO₂ alkyl containing 1 to 6 carbon atoms or tosyl.

The compounds of the foregoing formula may be synthesized in a conventional manner by treating a di- or triarylmethane compound possessing, for example, a lactone or sultone ring-closing moiety with phosphorus oxychloride or other suitable reagent to give the corresponding carbonyl or sulfonyl chloride followed by reacting with an ortho-phenylene diamine derivative and then with the appropriate chloroformate derivative to give the desired N-substituted lactam or sultam, by treating a di- or triarylmethane compound possessing an unsubstituted lactam or sultam ring-closing moiety with a base, such as sodium hydride, to give the corresponding lactam or sultam anion followed by reacting with an ortho-fluoro-nitrobenzene derivative, reducing the nitro group and finally reacting the resulting amino group with the appropriate chloroformate derivative to give the desired N-substituted lactam or sultam, or by reducing both the lactone and the dye to the leuco form followed by halogenating or tosylating the alcohol and reacting the latter compound with an ortho-substituted aniline derivative and then oxidizing the leuco dye to give the desired N-substituted benzylamine product. The following represents a schematic illustration of the above-described syntheses.

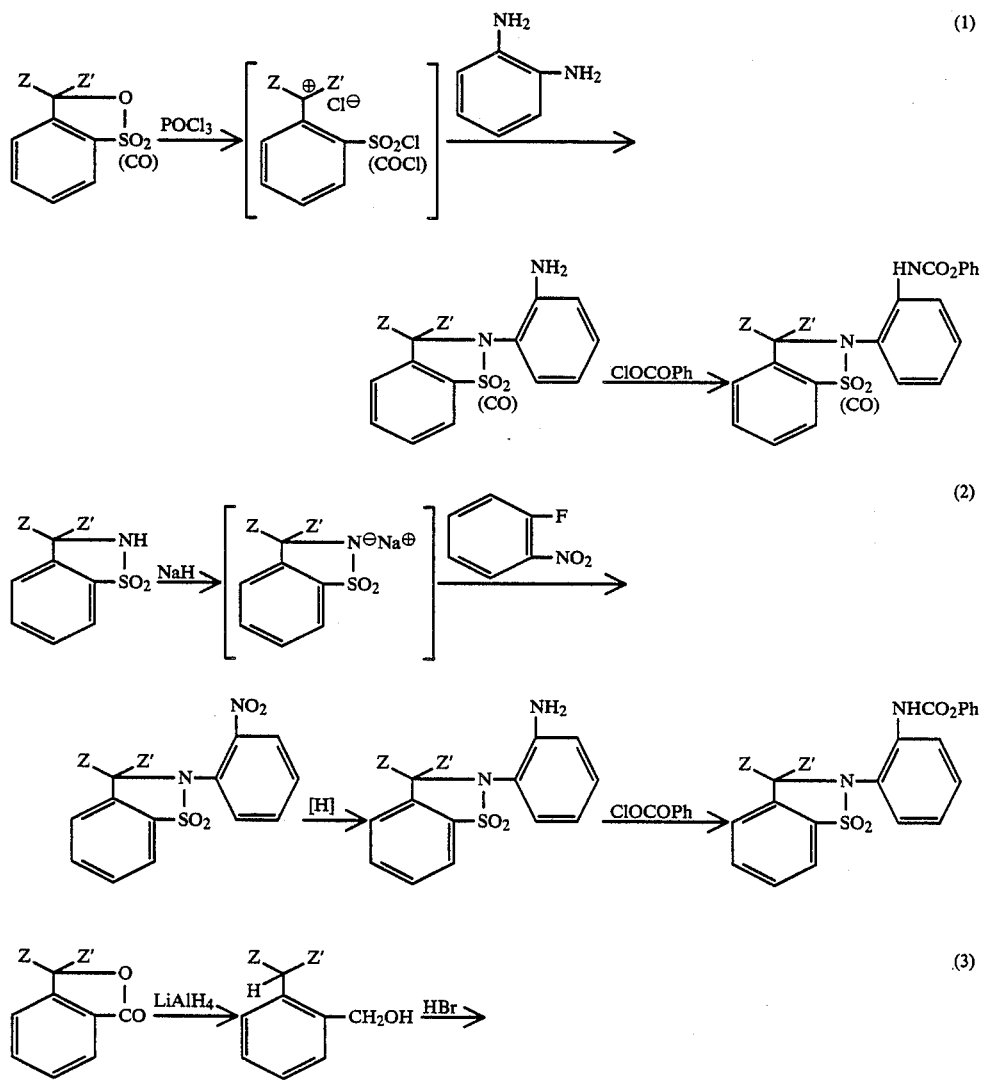

-continued

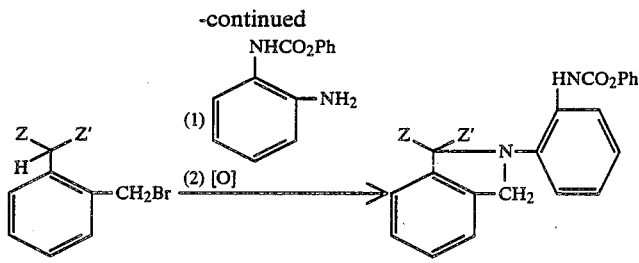

wherein Z and Z' have the same meaning given above.

Various diarylmethane and triarylmethane dyes including bridged triarylmethanes possessing, for example, a lactone or sultone ring-closing moiety or capable of being derivatized with these moieties have been disclosed in the art. For example, various such dyes have been described in Venkataraman, K., The Chemistry of Synthetic Dyes, Academic Press, Inc., New York, 1952, pp 705-760 and 1111 and in U.S. Pat. Nos. 3,491,111; 3,491,112; 3,491,116; 3,509,173; 3,509,174; 3,514,310, 3,514,311, 3,775,424, 3,853,869, 3,872,046, 3,931,227, 3,959,571, 4,341,403, 4,304,833, 4,354,017, 4,535,172 and 4,535,348.

If the starting materials possess hydroxy, carboxy, mercapto or other substituents that may require blocking during synthesis, conventional protecting groups may be employed as described by McOmie, J. F. W., Protective Groups in Organic Chemistry, Plenum Press, New York, 1973 and by Greene, Theodora W., Protective Groups in Organic Synthesis, John Wiley & Sons, New York, 1981.

The following examples are given to further illustrate the preparation of the foregoing compounds.

EXAMPLE 1

Preparation of the compound having the formula

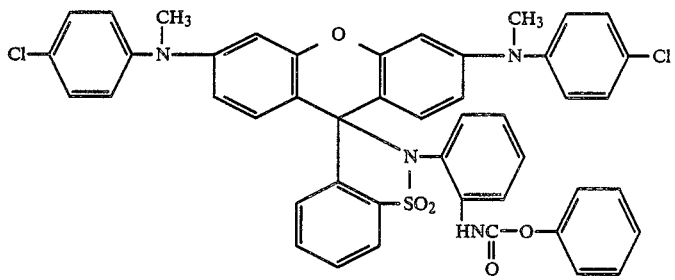

To 2.1 g of the compound having the formula

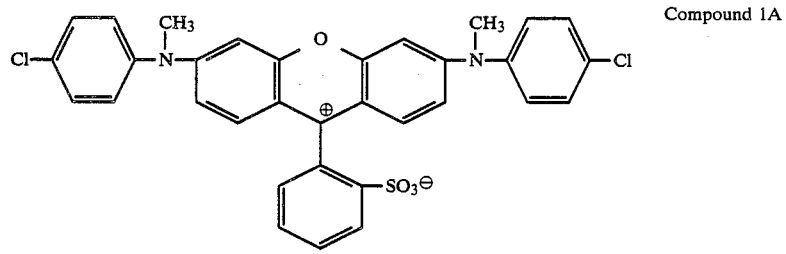

Compound 1A was added 30 ml of phosphorus oxychloride and the solution was stirred at 60° C. for about 4 hours. The excess phosphorus oxychloride was stripped off and the residue was treated with two 30 ml portions of toluene, each subsequently evaporated in a vacuum. The resulting solid was dissolved in methylene chloride and the resulting solution was added dropwise to 5 g of ortho-phenylene diamine and 440 mg of 4-dimethylaminopyridine dissolved in methylene chloride at ice bath temperature. After stirring overnight, the reaction mixture was combined with another reaction mixture prepared in substantially the same manner except that 5 g of Compound 1A, 75 ml of phosphorus oxychloride and 10 g of ortho-phenylene diamine were employed without the dimethylaminopyridine. The combined reaction mixtures were purified by high pressure liquid chromotography to yield 1.5 g of the following white compound.

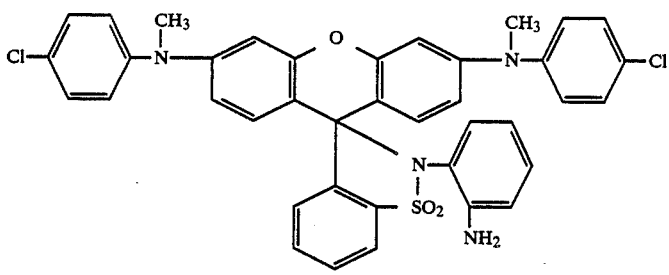

Compound 1B 0.5 gram of Compound 1B was dissolved in 6 ml of methylene chloride. Sodium bicarbonate (1 equivalent) was added and the resulting solution was stirred at room temperature vigorously while one equivalent (0.9 ml) of phenylchloroformate dissolved in 2 ml of methylene chloride was added dropwise. Another addition of 3 equivalents each of sodium bicarbonate and phenylchloroformate were required to drive the reaction to completion. Silica gel TLC of a sample using 25% ethylacetate in hexane showed that the reaction was substantially complete and gave a colorless compound that became intensely magenta upon heating. The reaction mixture was filtered, evaporated and redissolved in a small amount of methylene chloride for purification by silica gel medium pressure liquid chromotography to yield 500 mg of the title compound as a slightly pink solid. M/e+826.

EXAMPLE 2

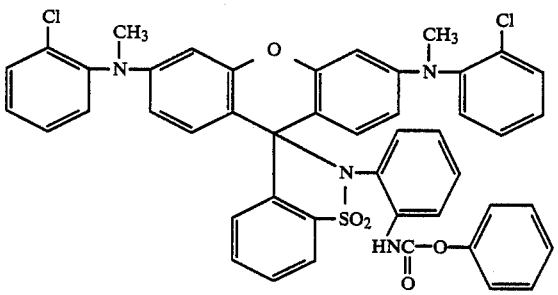

To a solution of 66 g (0.09 mole) of Compound 2A of the following formula dissolved in 450 ml of methylene chloride

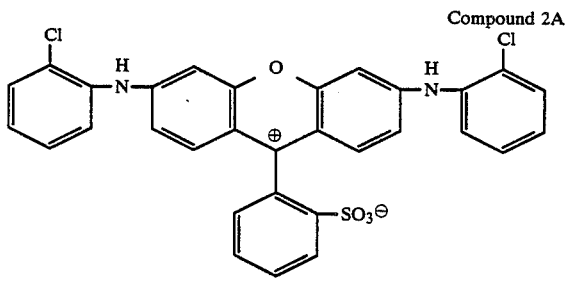

Compound 2A was added 20.56 ml (0.216 mole) of dimethyl sulfate and 3.06 g of tetrabutylammonium hydrogen sulfate. A sodium hydroxide solution, 9.24 g (0.231 mole) in 150 ml of water, was added to the reaction mixture dropwise over 90 minutes. The resulting mixture was stirred at room temperature for four hours after the addition was complete. Another solution of 16.5 g (0.42 mole) of sodium hydroxide in 280 ml of water was added in one portion to the reaction mixture which was then stirred for an additional five hours. The organic layer was separated and diluted with 330 ml of methylene chloride. This solution was then dried by distilling off approximately 300 ml of solvent and the residue comprising the corresponding bis N-methyl compound (Compound 2B) was cooled to room temperature.

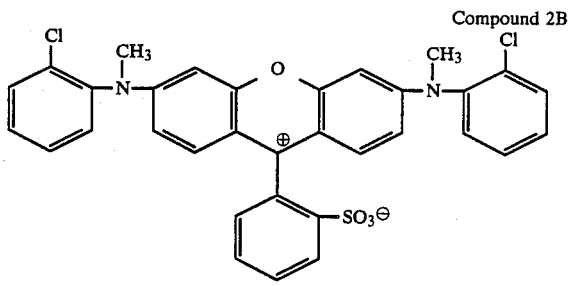

Compound 2B

To the dried residue (2B) was added 21.9 ml (0.234 mole) of phosphorus oxychloride and 1.5 ml (0.015 mole) of N-methylpyrrolidinone. The reaction mixture was heated to reflux and stirred for six hours and then cooled to room temperature. 22 g (0.18 mole) of 4-dimethylaminopyridine in a minimum amount of methylene chloride was added dropwise followed by the portionwise addition of 48 g (0.45 mole—5 equivalents) of o-phenylene diamine in 400 ml of methylene chloride over 30 minutes. The reaction temperature during and after addition was maintained between 20° and 25° C. The reaction was stirred at 20° C. for four hours and then at 40° C. for two hours. Silica gel TLC of a sample in 20% ethylacetate in hexane indicated that the reaction was substantially complete. The reaction mixture was filtered, reduced in volume to about 200 ml and purified by silica gel high pressure liquid chromatography to give the following compound.

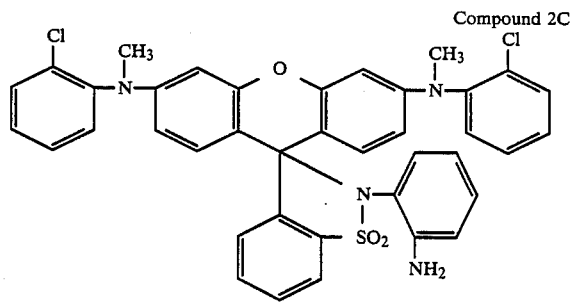

Compound 2C 4.2 grams (0.006 mole) of Compound 2C was dissolved in a minimum amount of methylene chloride and stirred briskly with 2 g. of sodium bicarbonate at room temperature under nitrogen. 3.0 ml of phenylchloroformate dissolved in a few mls of methylene chloride was added dropwise over 30 minutes. The reaction mixture turned an intense magenta color. After several hours of stirring, silica gel TLC of a sample using 25% ethylacetate in hexane showed substantially complete conversion to a new colorless compound which turned magenta upon heating the TLC plate to 130°–180° C. The reaction mixture was purified by silica gel chromotography (elution with hexane followed by 5%, 10%, 15%, 20%, 25% ethylacetate in hexane) to give the title compound as a light pink solid (3.74 g; 76% by weight yield). M/e+826

EXAMPLE 3

Preparation of the compound having the formula

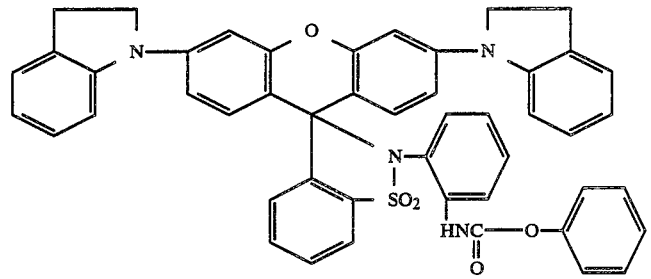

8 grams of the compound having the fomula

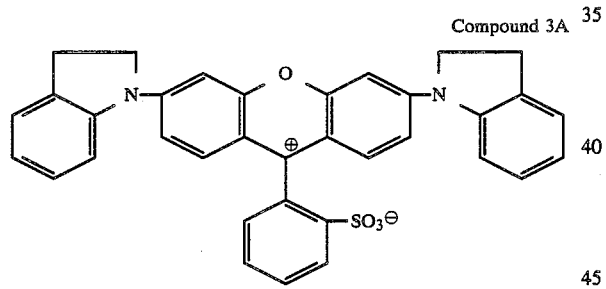

Compound 3A and 5.84 g of phosphorus oxychloride dissolved in 120 ml of chloroform were refluxed for 5 hours and then allowed to stand at room temperature overnight. The reaction mixture was stirred vigorously with 42 ml water for about 20 minutes, then transferred to a separatory funnel and the organic layer separated. The chloroform layer was washed twice with 50 ml portions of water then dried over magnesium sulfate. After filtering to remove the magnesium sulfate, the solution was cooled to 0° C. and 8.55 g of 4-dimethylaminopyridine was added portionwise over 10 minutes. A small amount of chloroform was added for dilution. Then 7.56 g of o-phenylene diamine dissolved in a minimum amount of chloroform was added dropwise to the solution over 30 minutes. The reaction mixture was allowed to come to room temperature and stirring was continued for 4 hours. The reaction mixture was filtered and the volume reduced to about 80 ml. The mixture was then injected onto a high pressure silica gel column and eluted with 2 liters of hexane followed by 2 liters each of 5% ethylacetate/hexane, 10% ethylacetate/hexane, 15% ethylacetate/hexane and 20% ethylacetate/hexane. 770 mg of the following compound was recovered.

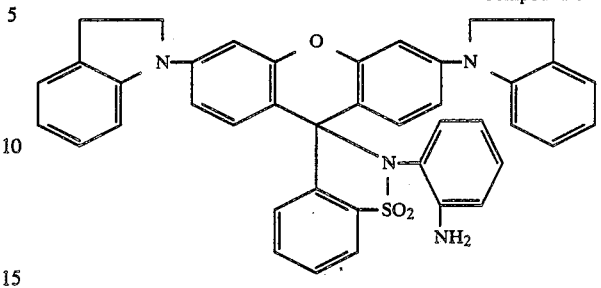

Compound 3B 770 mgs. of Compound 3B was dissolved in a minimum of methylene chloride. Sodium bicarbonate (4 equivalents) was added and the reaction mixture was stirred biskly under nitrogen. Four equivalents of phenylchloroformate was added dropwise over 30 minutes at room temperature and the reaction was allowed to stir overnight. The reaction mixture was filtered and applied to a medium pressure silica gel column conditioned with hexane and eluted with hexane, 5% ethylacetate/hexane, 10% ethylacetate/hexane, 15% ethylacetate/hexane and 20% ethylacetate/hexane. 340 mg of the title compound was recovered as a light greenish-white solid. M/e$^{30}$ 781

EXAMPLE 4

Preparation of the compound having the formula

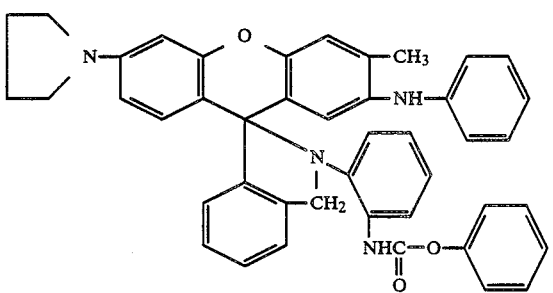

0.128 grams of the compound having the formula

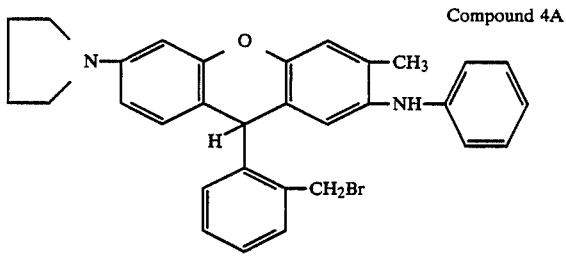

Compound 4A and 0.126 g of 2-carbophenoxyaminoaniline were mixed in approximately 3 ml of N-methylpyrrolidinone to give an amber solution. After two days at room temperature, the reaction mixture was added to 20 ml of saturated aqueous sodium chloride solution. The green-gray precipitate that formed, was filtered, washed with water and pressed partly dry before being dissolved in 30 ml methylene chloride. Sodium sulfate was added to the methylene chloride solution and after a brief drying period, the solution was filtered. The green filtrate was concentrated to about 20 ml and applied to a medium pressure silical gel column preconditioned with methylene chloride. The column was eluted with methylene chloride and 60 mgs of the following compound was recovered as a colorless oil.

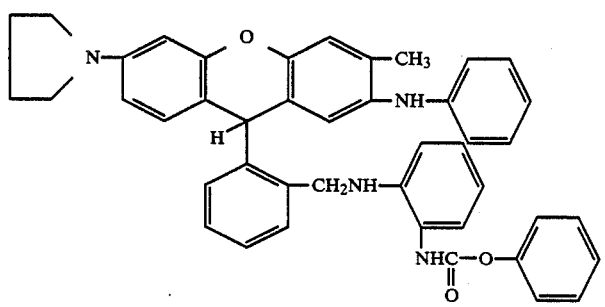

Compound 4B 60 mgs of the colorless oil obtained above was dissolved in 5 ml of methylene chloride and 24 mgs of o-chloranil was added giving a dark purple solution. After 10 minutes, TLC indicated that oxidation was complete. The reaction solution was applied to a gravity silica column preconditioned with 80:20 hexane/ethylacetate. The column was eluted with 80:20 hexane/ethylacetate and 20 mg of the title compound was recovered as a white solid. M/e+671

The aniline used in Example 4 above was prepared according to the procedure described in L. Raiford, E. Conrad and W. Coppock, J. Org. Chem. 7, pp. 346–53 (1942).

Compound 4A employed as the starting material in Example 4 was prepared from the commercially available lactone, Compound (i), as follows:

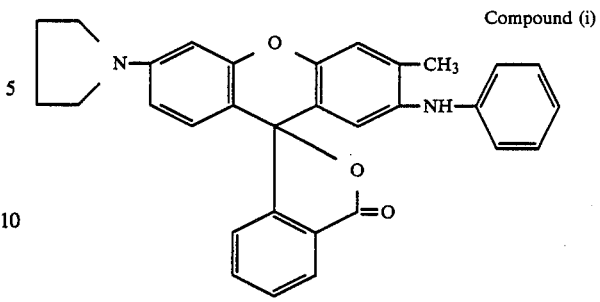

Compound (i)

A solution of 30 g of Compound (i) in 500 ml of dry tetrahydrofuran was added dropwise to a slurry of 37.9 g. of lithium aluminum hydride in 500 ml of tetrahydrofuran under a nitrogen atmosphere with rapid mechanical stirring during 40 minutes. The resulting mixture was refluxed for 40 minutes. After cooling to room temperature, an aliquot was examined by silica gel TLC which showed the reaction to be complete. The excess lithium aluminum hydride was destroyed by the dropwise addition of 100 ml of ethyl acetate to the reaction mixture at about 0° C. followed by 9.6 ml of water, 9.6 ml of 15% sodium hydroxide and finally 28.8 ml of water. The reaction mixture was filtered through Celite to yield an orange-yellow filtrate and the solvent removed under reduced pressure. The residue was crystallized from 150 ml of ethanol (absolute) to give 14.6 g of the following compound as orange crystals.

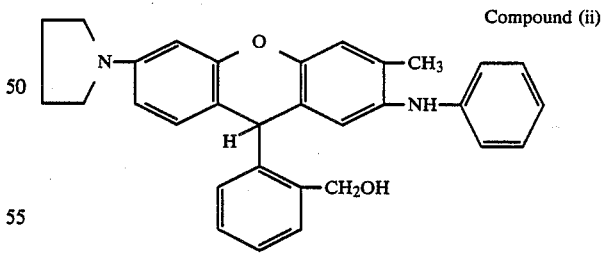

Compound (ii)

14.6 g of Compound (ii) was added to a saturated solution of hydrogen bromide in 75 ml of methanesulfonic acid under a nitrogen atmosphere at room temperature and stirred overnight. The reaction mixture was poured into 1,000 ml of water and the blue-gray precipitate collected by filtration. The pasty solids were dissolved in about 350 ml of methylene chloride and washed once with 200 ml of saturated sodium bicarbonate in water before drying the solution over sodium sulfate. The solution was filtered and the filtrate treated with 15 g of silica gel, filtered again and the solvent removed under reduced pressure to give 19.15 g of an orange solid. The solid was triturated with 100 ml of ether and filtered to yield 15.3 g of Compound 4A as a pale orange solid.

EXAMPLE 5

Preparation of the compound having the formula

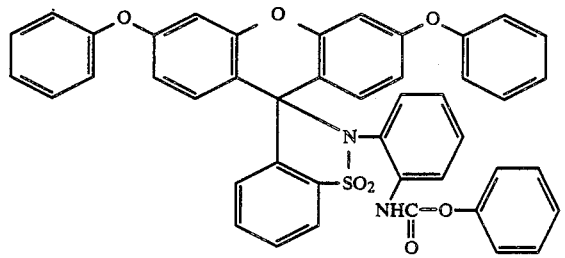

To 5.0 g of the compound having the formula

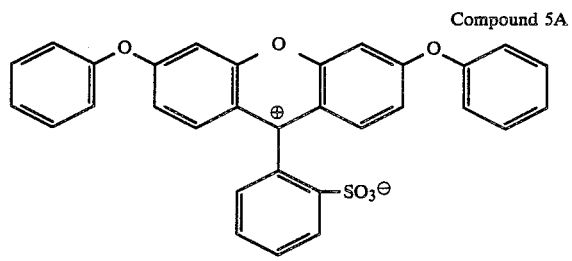

Compound 5A was added 40 ml of phosphorus oxychloride and the resulting solution was stirred at 70° C. in an oil bath for 6 hours and then allowed to stand overnight. The excess phosphorus oxychloride was removed by distillation and the residue treated with 75 ml of toluene. After removing the toluene, the residue was dissolved in 25 ml of dry tetrahydrofuran. To this solution was added 4.15 g of o-phenylenediamine dissolved in a minimum amount of tetrahydrofuran over 30 minutes at 20° C. After stirring overnight, the reaction mixture was filtered and the filtrate set aside. The solids collected by filtration were washed with a small amount of tetrahydrofuran and then washed repeatedly with water to give 3.11 g of an off-white solid comprising Compound 5B having the formula

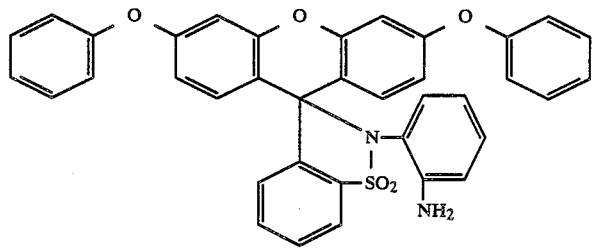

Compound 5B

A second crop of crude Compound 5B (about 700 mgs) was recovered from the filtrate set aside above.

The off-white solid obtained above (3.11 g) was dissolved in a minimum amount of methylene chloride and stirred vigorously with 3.11 g of sodium bicarbonate. Phenylchloroformate (2.56 ml) was added dropwise over 30 minutes and the reaction mixture allowed to stir overnight. TLC on silica gel using 25% ethylacetate/75% hexane indicated that a trace of starting material remained. An additional 0.5 ml of phenylchloroformate was added and stirring was continued for one hour. The reaction mixture was filtered through filter aid and combined with the filtrate obtained from the reaction of the second crop of Compound B (about 700 mg) with phenylchloroformate in the presence of sodium bicarbonate. The combined methylene chloride filtrates were reduced to about 15 ml. Solids began to form. About 10 ml of methylene chloride was added and the mixture stirred gently while more solids formed. The mixture was filtered and the solids collected were stirred vigorously in 40 ml of hexane. The hexane mixture was filtered giving 1.56 g of the title compound as an off-white solid. The filtrate was then slurried with 100 ml hexane, stirred for several hours and filtered to give an additional 1.32 g of the title compound as a light yellow solid. $M/e^+$ 731

The starting material, Compound 5A, used above was synthesized as follows.

(i) 3,6-Dichlorosulfofluorescein (3.0 g, 7.40 mmole) and 4 equivalents of sodium phenolate (3.44 g, 29.6 mmole) were combined in approximately 6 ml of dry N-methylpyrrolidinone and stirred under nitrogen at 110° C. for 2 hours. The mixture was heated to 160° C. briefly, allowed to cool and poured slowly into a mixture of ice and 1N hydrochloric acid with good stirring. The precipitate was filtered off, washed well with water, taken up in methylene chloride, dried over sodium sulfate, filtered and evaporated.

The material was subjected to flash chromatography on silica gel using successive elutions of methylene chloride with 2% methanol, 5% methanol and 10% methanol. The 5% methanol in methylene chloride elution gave the purest fraction of the compound of the formula

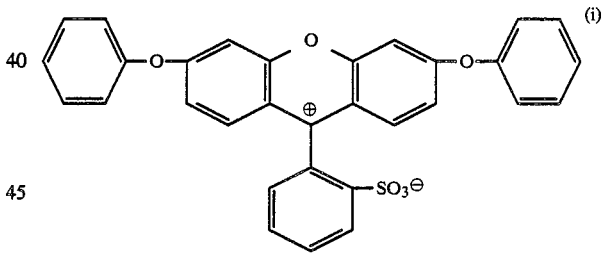

(i)

having a bright yellow spot at $R_f$ 0.35 (3% methanol in methylene chloride) 1.28 g (33% yield), $\lambda_{max}$ 440 nm as measured in methanol.

EXAMPLE 6

Preparation of the compound having the formula

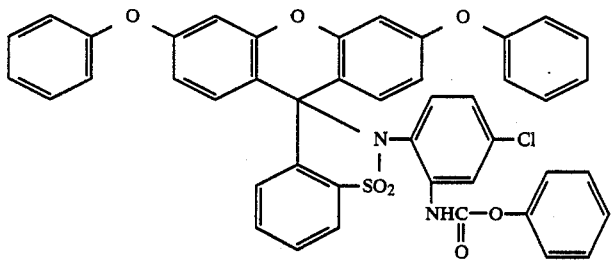

The title compound was prepared according to the procedure of Example 5 above using 4-chloro-1,2-phenylenediamine instead of o-phenylenediamine.

EXAMPLE 7

Preparation of the compound having the formula

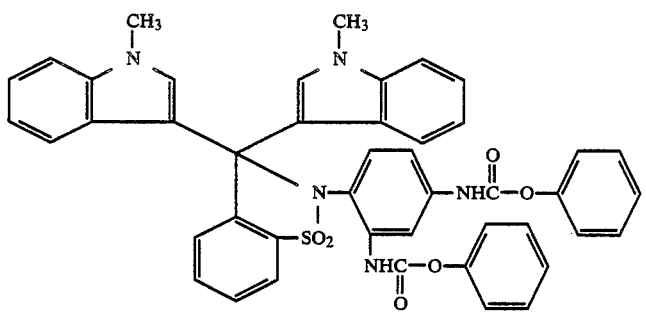

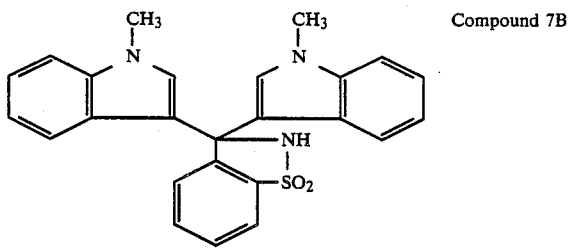

Compound 7B

A mixture of o-sulfobenzoic acid anhydride (0.5 g, 0.0027 mol), 1-methylindole (0.73 ml, 0.057 mol) and a trace of p-toluenesulfonic acid in 25 ml of dry toluene were refluxed with removal of generated water until the starting materials were consumed as indicated by TLC on silica gel using 15% methanol in methylene chloride. The cherry red product, Compound 7A, was purified by column chromatography.

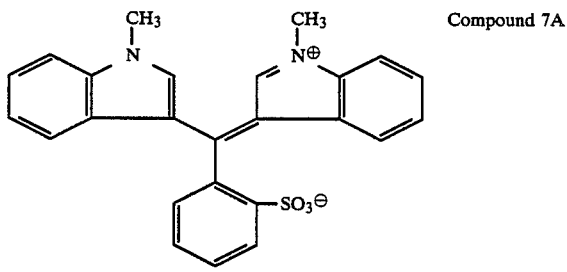

Compound 7A

Compound 7A (0.6 g, 0.0014 mol) was refluxed with phosphorus oxychloride (9 ml). Excess phosphorus oxychloride was removed under reduced pressure, and the residue (in methylene chloride) treated with gaseous ammonia. The sultam product, Compound 7B, was obtained as a lemon-yellow crystalline substance (0.3 g, 60% yield); M/e (fd) 428.

The sultam (0.21 g., 0.00049 mol) was treated with an equivalent of sodium hydride in dry dimethylsulfoxide. 1-Fluoro-2,4-dinitrobenzene (one equivalent) was added, and work-up provided 0.24 g of a dull red solid, Compound 7C having the formula:

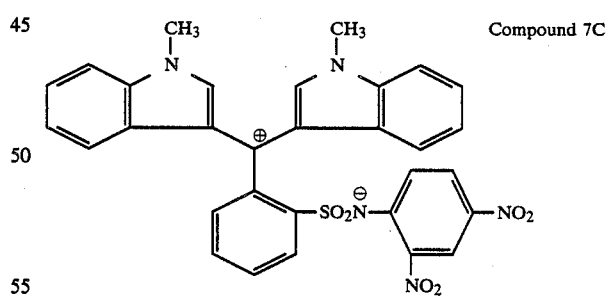

Compound 7C

Compound 7C (0.24 g, 0.0004 mol) was reduced to the corresponding diamino compound with stannous chloride (7.4 equivalents) in N,N-dimethylformamide at 55°-60° C. Basic work-up provided 50 mg of an orange-yellow syrup (TLC: 5% methanol/methylenechloride). (Most of the reduction product remained complexed with tin, 730 mg. solid, which was used directly in the following step.)

The reduction product of Compound 7C (0.05 g, 0.000094 mol) was treated with 2.5 equivalents of phenylchloroformate in the presence of sodium bicarbonate in methylene chloride. The title compound was isolated from the reaction mixture by thin layer chromatography (2% acetonitrile/methylene chloride) as a colorless substance.

EXAMPLE 8

Preparation of the compound having the formula

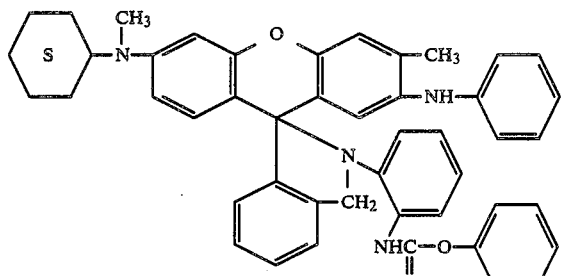

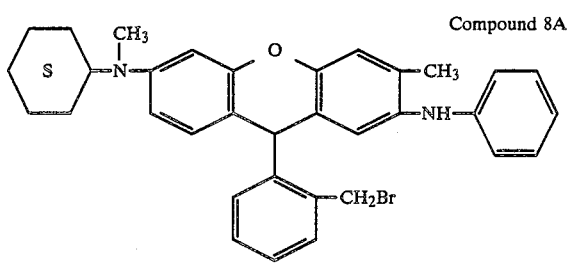

The title compound was prepared according to the procedure given in Example 4 above using Compound 8A as the starting material.

Compound 8A was synthesized from the corresponding lactone as described in Example 4.

Illustrative of other compounds of the present invention are those of the following formulae:

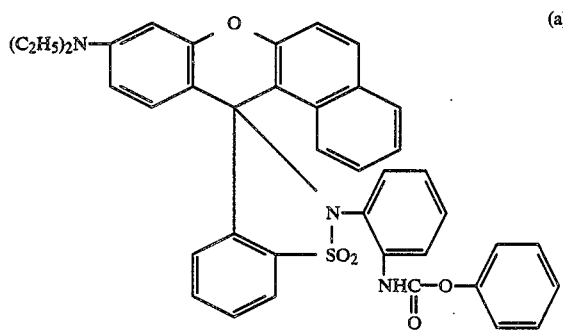
(a)

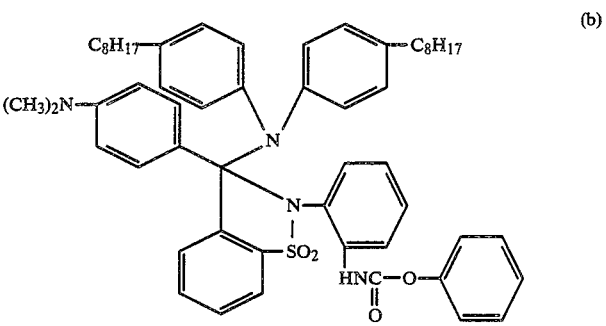
(b)

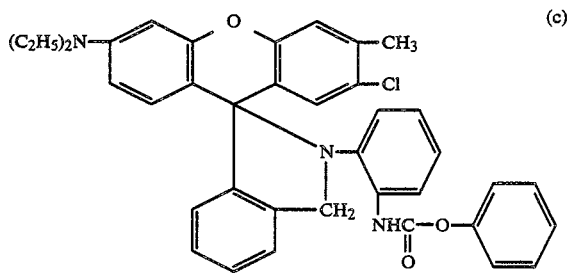
(c)

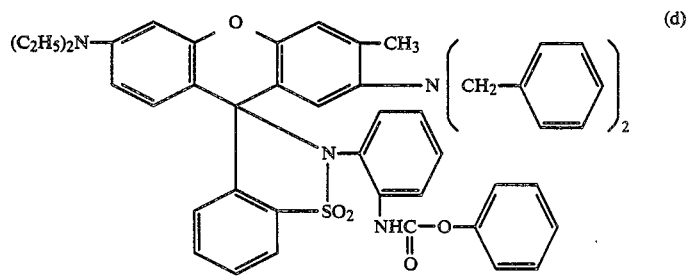
(d)

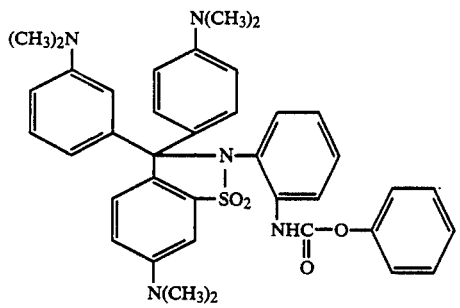 (e)

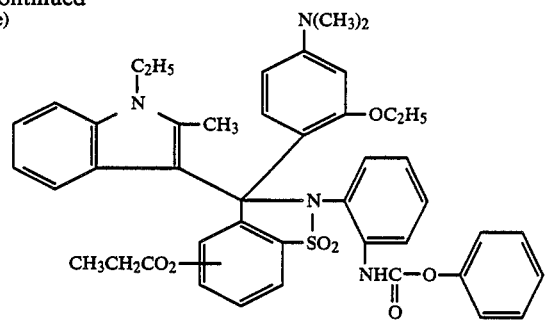 (f)

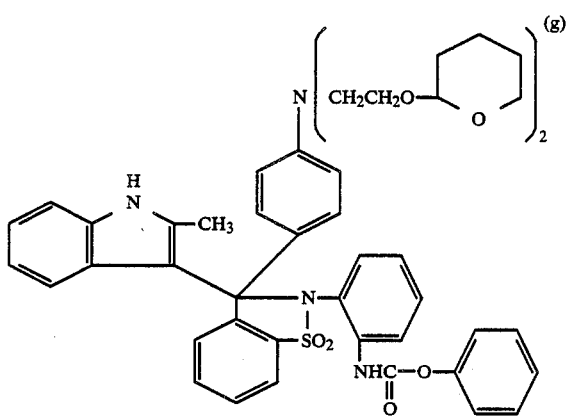 (g)

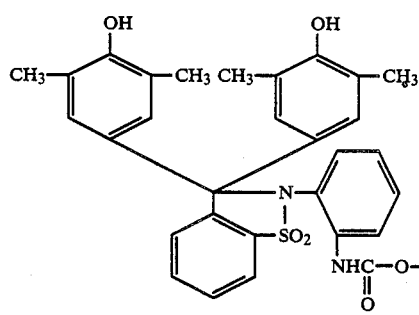 (h)

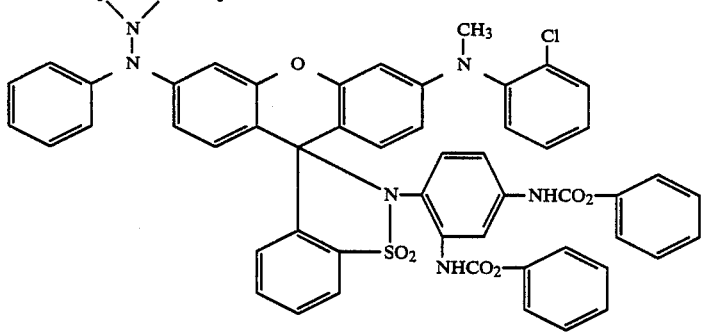 (i)

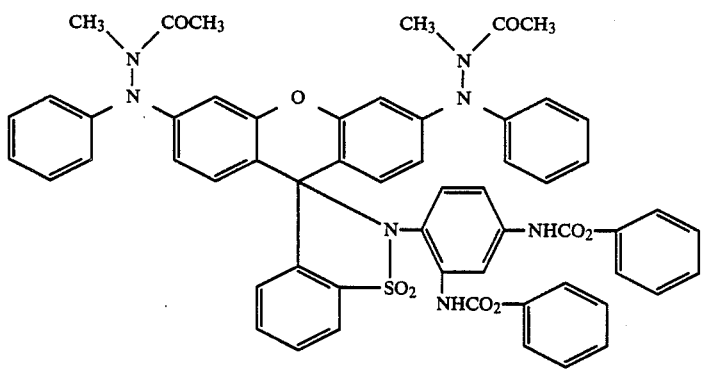 (j)

In producing images according to the present invention, the way in which the heat is applied or induced imagewise may be realized in a variety of ways, for example, by direct application of heat using a thermal printing head or thermal recording pen or by conduction from heated image-markings of an original using conventional thermographic copying techniques. Preferably, selective heating is produced in the image-forming layers by the conversion of electromagnetic radiation into heat and preferably, the light source is a laser beam emitting source such as a gas laser or semiconductor laser diode. The use of a laser beam is not only well suited for recording in a scanning mode but by utilizing a highly concentrated beam, photo-energy can be concentrated in a small area so that it is possible to record at high speed and high density. Also, it is a convenient way to record data as a heat pattern in response to transmitted signals such as digitized information and a convenient way of preparing multicolor images by employing a plurality of laser beam sources that emit laser beams of different wavelengths.

In the latter embodiment an infra-red absorbing substance is employed for converting infra-red radiation into heat which is transferred to the colorless di- or triarylmethane compound to initiate the fragmentation of the masked acyl group thereby effecting the intramolecular acylation reaction to form color imagewise. Obviously, the infra-red absorber should be in heat-conductive relationship with the heat-sensitive compound, for example, in the same layer as the heat-sensitive compound or in an adjacent layer. Preferably, the infra-red absorber is an organic compound, such as, a cyanine, merocyanine or thiopyrylium dye and preferable, is substantially non-absorbing in the visible region of the electromagnetic spectrum so that it will not add any substantial amount of color to the $D_{min}$ areas, i.e., the highlight areas of the image.

In the production of multicolor images, infra-red absorbers may be selected that absorb radiation at different predetermined wavelengths above 700 nm, which wavelengths are at least about 60 nm apart, so that each imaging layer may be exposed separately and independently of the others by using infra-red radiation at the particular wavelengths selectively absorbed by the respective infra-red absorbers. As an illustration, the layers of heat-sensitive compound for forming yellow, magenta and cyan may have infra-red absorbers associated therewith that absorb radiation at 760 nm, 820 nm and 1100 nm, respectively, and may be addressed by laser beam sources, for example, infra-red laser diodes emitting laser beams at these respective wavelengths so that the yellow imaging layer can be exposed independently of the magenta and cyan imaging layers, the magenta imaging layer can be exposed independently of the yellow and cyan imaging layers, and the cyan imaging layer can be exposed independently of the yellow and magenta imaging layers. While each layer may be exposed in a separate scan, it is usually preferred to expose all of the imaging layers simultaneously in a single scan using multiple laser beam sources of the appropriate wavelengths. Rather than using superimposed imaging layers, the heat-sensitive compounds and associated infra-red absorbers may be arranged in an array of side-by-side dots or stripes in a single recording layer.

In a further embodiment, multicolor images may be produced using the same infra-red absorbing compound in association with each of two or more superposed imaging layers and exposing each imaging layer by controlling the depth of focussing of the laser beam. In this embodiment, the concentration of infra-red absorber is adjusted so that each of the infra-red absorbing layers absorb approximately the same amount of laser beam energy. For example, where there are three infrared absorbing layers, each layer would absorb about one-third of the laser beam energy. It will be appreciated that controlling the focussing depth to address each layer separately may be carried out in combination with the previous embodiment of using infra-red absorbers that selectively absorb at different wavelengths in which instance the concentration of infra-red absorber would not have to be adjusted for the laser beam energy since the first infra-red dye would not absorb any substantial amount of radiation at the absorption peaks of the second and third dyes and so forth.

Where imagewise heating is induced by converting light to heat as in the embodiments described above, the heat-sensitive element may be heated prior to or during imagewise heating. This may be achieved using a heating platen or heated drum or by employing an additional laser beam source for heating the element while it is being exposed imagewise.

The heat-sensitive elements of the present invention comprise a support carrying at least one imaging layer of the above-denoted heat-sensitive compounds and may contain additional layers, for example, a subbing layer to improve adhesion to the support, interlayers for thermally isolating the imaging layers from each other, infra-red absorbing layers as discussed above, anti-static layers, an anti-abrasive topcoat layer which also may function as a UV protecting layer by including an ultraviolet absorber therein or other auxiliary layers. For example, an electroconductive layer may be included and imagewise color formation effected by heat energy in response to an electrical signal.

The heat-sensitive compounds are selected to give the desired color or combination of colors, and for multicolor images, the compounds selected may comprise the additive primary colors red, green and blue, the subtractive primaries yellow, magenta and cyan or other combinations of colors, which combinations may additionally include black. As noted previously, the compounds generally are selected to give the subtractive colors cyan, magenta and yellow as commonly employed in photographic processes to provide full natural color. Also, a triarylmethane compound that forms a black dye can be selected for providing a black image.

The support employed may be transparent or opaque and may be any material that retains its dimensional stability at the temperature used for image formation. Suitable supports include paper, paper coated with a resin or pigment, such as, calcium carbonate or calcined clay, synthetic papers or plastic films, such as polyethylene, polypropylene, polycarbonate, cellulose acetate, polyethylene terephthalate and polystyrene.

Usually the layer of heat-sensitive compound contains a binder and is formed by combining the heat-sensitive compound and a binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking where thermal recording heads or thermal pens are used to apply the imagewise pattern of heat. In forming the layer(s) containing the heat-sensitive compounds and the interlayers or other layers, temperatures should be maintained below levels that will initiate the fragmentation reaction so that the heat-sensitive compounds will not be prematurely colored.

Any of the binders commonly employed in heat-sensitive recording elements may be employed provided that the binder selected is inert, i.e., does not have any adverse effect on the heat-sensitive compound incorporated therein. Also, the binder should be heat-stable at the temperatures encountered during image formation and it should be transparent so that it does not interfere with viewing of the color image. Where electromagnetic radiation is employed to induce imagewise heating, the binder also should transmit the light intended to initiate image formation. Examples of binders that may be used include polyvinyl alcohol, polyvinyl pyrrolidone, methyl cellulose, cellulose acetate butyrate, copolymers of styrene and butadiene, polymethyl methacrylate, copolymers of methyl and ethyl acrylate, polyvinyl acetate, polyvinyl chloride and polyvinyl butyral.

In addition to the above-mentioned reagents, it is desirable to include an acidic substance, for example, salicyclic acid or a phenol, such as, a resorcinal in the layer of heat-sensitive compound when using compounds, such as those of Examples 5 and 6 in order to enhance color formation.

As an illustration of the thermal "coloration" of the compounds of the present invention, the compounds of Examples 1 to 3 were coated on a polyethylene terephthalate support by combining the compound and a binder and an infra-red absorber in a solvent, applying a layer of the coating composition to the support and then drying the coating. The formulations used for the coatings are set forth below.

1.
   25.0 mgs. Compound of Example 1
   0.5 cc 2% polyvinylbutyral in tetrahydrofuran
   0.5 cc tetrahydrofuran
   3.0 mgs. infra-red absorber 2.
   40.0 mgs. Compound of Example 2
   1.0 cc 2% polymethylmethacrylate in ethyl acetate
   4.0 mgs. infra-red absorber 3.
   30.0 mgs. Compound of Example 3
   1.0 cc tetrahydrofuran
   20.0 mgs. cellulose acetate butyrate
   4.0 mgs. infra-red absorber Coating composition 1 was applied to the support using a #16 Meyer Rod and coating compositions 2 and 3 were applied to the support using a #8 Meyer Rod.

The infra-red absorber used in coating compositions 1, 2 and 3 was the compound having the formula

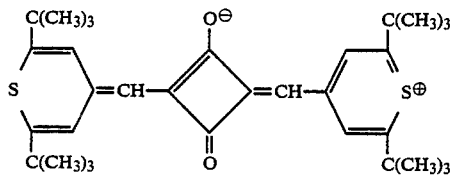

The coated samples were irradiated using a laser diode emitting at a wavelength of 824 nm and at an output of 20 mWatts which was varied between 1.9 and 11.3 mWatts at the film plane to determine the energy level required to fully colorize the sample. It was found for all of the coated samples that 5.8 mWatts at the film plane at a scanning rate of 0.125 microns per microsecond made a fully colored 5 micron track. The coated samples 1 and 2 were converted from substantially colorless to magenta and the coated sample 3 was converted from substantially colorless to cyan.

The compound of Example 5 was mixed with salicylic acid (about 3:1 vol/vol), and this mixture of solids was dissolved in tetrahydrofuran. To the tetrahydrofuran solution was added a solution of polyvinyl pyrrolidone in acetonitrile (about 1:1 vol/vol). The resulting coating solution was then applied to two glass slides, the coatings dried and the coated slides covered with another glass slide. One of the covered coated slides was heated to about 150° to 200° C. and the other was set aside at room temperature as a control. The coating on the heated slide underwent coloration to yellow whereas the room temperature control showed no change.

In a further experiment to demonstrate the enhanced coloration by employing an electron-withdrawing group as E, 1 mg. of each of the compounds of Examples 5 and 6 was placed at the ends of a glass slide and covered with another glass slide. The covered slide was then placed on a hot plate preheated to 180° C. Within about one minute, the compound of Example 6 began to form color and upon slowly increasing the temperature to about 250°-260° C., the compound of Example 6 appeared to be fully colored (bright yellow) at about 200° C. The compound of Example 5 showed no change (white) upon heating to about 250°-260° C.

The proposed structures for the colored form obtained upon heating the compounds of Examples 1, 2, 3, 5 and 6 and the phenol formed upon thermal fragmentation of the blocked acylation group are set out below together with the data obtained by mass spectroscopy for the initial colorless compound and for the colored form, the proposed structure of the colored form being suggested by this data.

-continued

| Compound | Colored Form | Phenol |
|---|---|---|
| Ex. 2<br>M/e+ 826 | 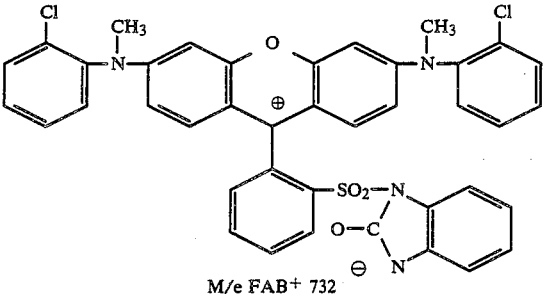<br>M/e FAB+ 732 | 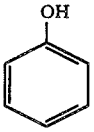 |
| Ex. 3<br>M/e+ 781 | 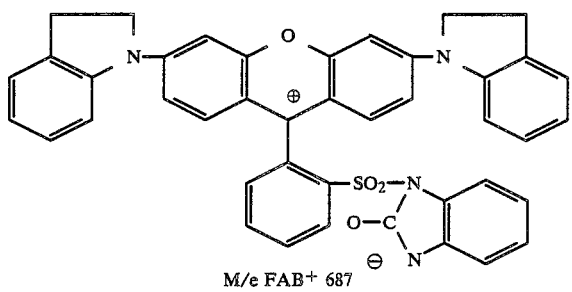<br>M/e FAB+ 687 | 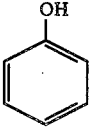 |
| Ex. 5<br>M/e+ 731 | 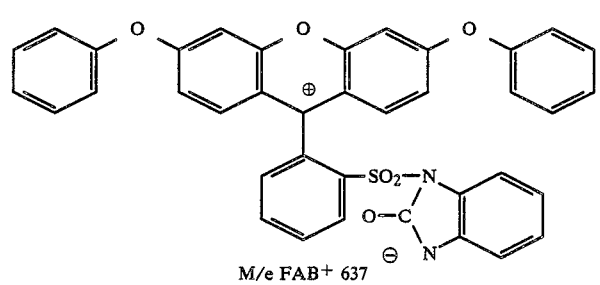<br>M/e FAB+ 637 | 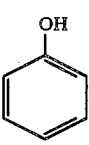 |
| Ex. 6<br>M/e+ 765 | 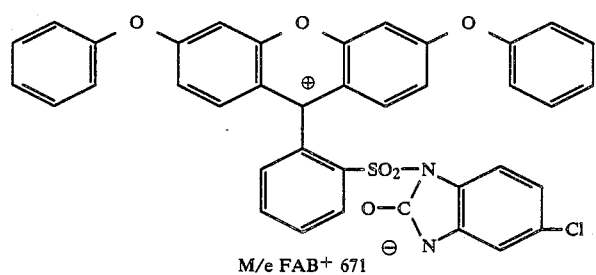<br>M/e FAB+ 671 | 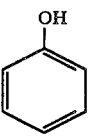 |

Using the compound of Example 2, the phenol formed upon heating was confirmed by thin layer chromatography as compared to an authentic sample.

Since certain changes may be made in the herein described subject matter without departing from the scope of the invention herein involved, it is intended that all matter contained in the above description and examples be interpreted as illustrative and not in a limiting sense.

What is claimed is:

1. A heat-sensitive element comprising a support carrying at least one imaging layer of a substantially colorless di- or triarylmethane imaging compound possessing within its di- or triarylmethane structure an aryl group substituted in the ortho position to the meso carbon atom with a moiety ring-closed on the meso carbon atom to form a 5- or 6-membered ring, said moiety possessing a nitrogen atom bonded directly to said meso carbon atom and said nitrogen atom being bound to a group with a masked acyl substituent that undergoes fragmentation upon heating to liberate the acyl group for effecting intramolecular acylation of said nitrogen atom to form a new group in the ortho position that cannot bond to the meso carbon atom whereby said di- or triarylmethane compound is rendered colored.

2. A heat-sensitive element as defined in claim 1 wherein an infra-red absorber is associated with said imaging layer of colorless imaging compound for absorbing radiation at wavelengths above 700 nm and transferring said absorbed radiation as heat to said compound.

3. A heat-sensitive element as defined in claim 1 wherein said colorless imaging compound upon heating is rendered black.

4. A heat-sensitive element as defined in claim 1 which comprises at least two said imaging layers of colorless imaging compound.

5. A heat-sensitive element as defined in claim 3 wherein each said imaging layer of colorless imaging compound has an infra-red absorber associated therewith for absorbing radiation at wavelengths above 700 nm and transferring said absorbed radiation as heat to said compound.

6. A heat-sensitive element as defined in claim 5 wherein said infra-red absorbers associated with said imaging layers selectively absorb radiation at different predetermined wavelengths above 700 nm.

7. A heat-sensitive element as defined in claim 5 wherein said infra-red absorbers associated with said imaging layers absorb radiation at the same wavelength above 700 nm.

8. A heat-sensitive element as defined in claim 5 which additionally includes a thermal isolation layer between adjacent imaging layers.

9. A heat-sensitive element as defined in claim 8 wherein said support carries an imaging layer of colorless imaging compound for forming a cyan image, an imaging layer of colorless imaging compound for forming a magenta image and an imaging layer of colorless imaging compound for forming a yellow image.

10. A method of thermal imaging which comprises heating imagewise a heat-sensitive element comprising a support carrying at least one imaging layer of a substantially colorless di- or triarylmethane imaging compound possessing within its triarylmethane structure an aryl group substituted in the ortho position to the meso carbon atom with a moiety ring-closed on the meso carbon atom to form a 5- or 6-membered ring, said moiety possessing a nitrogen atom bonded directly to said meso carbon atom and said nitrogen atom being bound to a group with a masked acyl substituent that undergoes fragmentation upon heating to liberate the acyl group for effecting intramolecular acylation of said nitrogen atom to form a new group in the ortho position that cannot bond to the meso carbon atom, said imagewise heating effecting the formation of said new group in the ortho position whereby said di- or triarylmethane compound is rendered colored in an imagewise pattern corresponding to said imagewise heating.

11. A method of thermal imaging as defined in claim 10 wherein an infra-red absorber is associated with said imaging layer of colorless imaging compound for absorbing radiation at wavelengths above 700 nm and transferring said absorbed radiation as heat to said compound, said layer being heated imagewise by imagewise exposure to infra-red radiation at a wavelength strongly absorbed by said infra-red absorber.

12. A method of thermal imaging as defined in claim 11 wherein said imaging layer is heated imagewise by imagewise exposure to a laser beam source emitting infra-red radiation at a wavelength strongly absorbed by said infra-red absorber.

13. A method of thermal imaging as defined in claim 10 wherein said element comprises at least two said imaging layers.

14. A method of thermal imaging as defined in claim 13 wherein said heat-sensitive element additionally includes a thermal isolation layer between adjacent imaging layers.

15. A method of thermal imaging as defined in claim 13 wherein an infra-red absorber is associated with each said imaging layer for absorbing radiation at wavelengths above 700 nm and transferring said absorbed radiation as heat to each said colorless imaging compound, said infra-red absorbers associated with said imaging layers selectively asorbing infra-red radiation at different predetermined wavelengths above 700 nm, said imagewise heating being effected by imagewise exposure to a plurality of laser beam sources emitting infra-red radiation at the respective wavelengths selectively absorbed by said infra-red absorbers.

16. A method of thermal imaging as defined in claim 13 wherein an infra-red absorber is associated with each said imaging layer for absorbing radiation at wavelengths above 700 nm and transferring said absorbed radiation as heat to each said colorless imaging compound, said infra-red absorbers associated with said imaging layers absorbing infra-red radiation at the same wavelength or at different wavelengths above 700 nm, said imaging layers being heated imagewise by adjusting the depth of focus of a laser beam source emitting radiation at the wavelength absorbed by said infra-red absorber.

* * * * *